United States Patent
Peyman

(10) Patent No.: US 6,489,335 B2
(45) Date of Patent: *Dec. 3, 2002

(54) TREATMENT OF OCULAR DISEASE

(76) Inventor: Gholam A. Peyman, 8654 Pontchartrain Blvd., Apt. 1, New Orleans, LA (US) 70124

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/507,076

(22) Filed: Feb. 18, 2000

(65) Prior Publication Data

US 2002/0013340 A1 Jan. 31, 2002

(51) Int. Cl.[7] .......................... A61K 31/44; A61K 31/38
(52) U.S. Cl. .......................... 514/291; 514/443; 514/912
(58) Field of Search ................................ 514/443, 912, 514/291

(56) References Cited

U.S. PATENT DOCUMENTS

| | | | |
|---|---|---|---|
| 5,457,182 A | * 10/1995 | Wiederrecht et al. | 530/402 |
| 5,770,607 A | 6/1998 | Honbo et al. | 514/302 |
| 5,952,371 A | 9/1999 | Baker et al. | 514/443 |
| 6,004,565 A | * 12/1999 | Chiba et al. | 424/278.1 |

OTHER PUBLICATIONS

Gholam A. Peyman, et al., *Keratitis (Noninfectious)*, Principles and Practice of Ophthalmology, W.B. Saunders Company, 1980, pp. 446–449.

Graeme M. Lipper, et al., *Recent therapeutic advances in dermatology*, JAMA, vol. 283, No. 2, Jan. 12, 2000, pp. 175–177.

Eric D. Donnenfeld, et al., *Cyclosporine provides effective treatment for dry eye*, Therapeutic Updates in Opthalmology, Special Issue, Jul. 1999, pp. 1–3.

Maxine Lipner, *Dry Eye 101: Developing etiologies and treatments for the widespread syndrome*, EyeWorld, Feb. 1999, pp. 19ff.

Jeffrey P. Gilbard, *EW Interview: Electrolyte balance is key to dry–eye product's success*, EyeWorld, Feb. 1999, pp. 20ff.

* cited by examiner

*Primary Examiner*—Zohreh Fay
(74) *Attorney, Agent, or Firm*—Wood, Herron & Evans, L.L.P.

(57) ABSTRACT

A formulation to treat ocular disease such as dry eye disease, as well as other diseases, is disclosed. Tacrolimus is administered either topically or by injection. For topical administration, an amount of about 1 ng to 10 μg may be formulated in an aqueous based cream that may be applied at bedtime or throughout the day. For injection, a dose of about 20–1000 μg/ml is used. Tacrolimus may also be administered in milligram quantities as a surgical implant contained in a diffusible walled reservoir sutured to the wall of the sclera, or may be contained within an inert carrier such as microspheres or liposomes to provide a slow-release drug delivery system.

19 Claims, No Drawings

TREATMENT OF OCULAR DISEASE

FIELD OF THE INVENTION

The invention is directed to therapeutic treatment of ocular diseases such as dry eye disease.

BACKGROUND

Dry eye disease encompasses any condition where the tear film loses water and becomes more concentrated. It is a common complaint, affecting three million people in the United States alone, yet it is difficult to diagnose and treat. The loss of water from the tear film causes a corresponding rise in tear osmolarity. The increased osmolarity results in symptoms such as a sandy-gritty feeling in the eye, burning, irritation, or a foreign-body sensation that worsens during the day. Patients suffering from dry eye disease complain of mild to severe symptoms, with signs ranging from minimal superficial punctate keratitis to corneal perforation.

Dry eye disease has a chronic remitting and relapsing nature and may result from a number of factors. The disease may be a natural part of the aging process, affecting 15%–20% of adults over age 40. It may also result from pathological processes such as diseases of the lacrimal glands, mucus glands, and/or lipid producing glands, and may occur with cell infiltration or atrophy of the lacrimal gland (Sjogren's Syndrome). Estrogen deficiency in post-menopausal women is also postulated to result in dry eye disease.

One method to treat dry eye disease is by topical administration of over-the-counter drugs that serve as artificial tears. Numerous varieties of these artificial tears are available (TheraTears® (Advanced Vision Research), Refresh® and Celluvisc® (Allergan), Tears Natural® and Bion Tears® (Alcon), GenTeal® and HypoTears® (CIBA Vision), each of which contain electrolytes and has varying pH levels, osmolarities, and surface tensions. Another method to treat dry eye disease is by surgery to close the lacrimal drainage ducts using punctum plugs. Neither method, however, is completely desirable. Artificial tears do not have a constant flow rate as do human tears, and treat the symptoms rather the cause of the disease. Surgery has its attendant risks, and may not be a viable option in older patients.

It is known that Cyclosporin A (cyclosporine, Allergan Inc.), may treat dry eye disease since patients administered cyclosporine for other disorders have shown a marked increase in tear flow. A topical formulation containing Cyclosporin A (Arrestase®, Allergan Inc.) is currently under review by the Food and Drug Administration. Cyclosporin A is an immunomodulator, suggesting that immune-mediated inflammation contributes to dry eye disease. Cyclosporin A has been used to treat various ocular pathologies such as glaucoma, corticosteroid-induced ocular hypertension, allograft rejection, infections, and ocular surface disease. It is also known that Cyclosporin A may be used in the eye to treat uveitis (inflammation of the uvea) by topical, intravitreal or systemic administration. Doses of 0.05%, 0.1%, and 0.5% cyclosporine have been reported. Cyclosporin A has good penetration into the cornea but not into the anterior chamber, and does not increase intraocular pressure or cause cataracts.

Tacrolimus (Prograf®, previously known as FK-506) is an immunomodulating drug that has been applied topically to treat a variety of dermatoses. Topical administration of tacrolimus at doses ranging from 0.03%–0.3% resulted in significant clinical improvement in atopic dermatitis after 2–3 weeks treatment, and tacrolimus treatment of other dermatologic diseases shows promise. Tacrolimus, like cyclosporine, blocks the signal transduction pathway needed to induce interleukin-2 gene expression and thereby activate T lymphocytes. In addition to suppressing T cell activation, tacrolimus inhibits anti-lgE-triggered histamine release and inhibits prostaglandin D2 synthesis in human skin mast cells. While oral administration produces limiting adverse effects (systemic immunosuppression, infection, neural toxicity, nephrotoxicity, and hypertension), topical administration for treatment of dermatoses at concentrations up to 0.3% showed no significant difference in effects between treated and control groups. In addition, tacrolimus is well tolerated locally and only occasionally causes mild irritation.

The non-systemic use of tacrolimus in the treatment of ocular diseases including dry eye disease would be advantageous.

SUMMARY OF THE INVENTION

The invention is directed to a method of treating ocular disease, such as dry eye disease, uveitis, scleritis, neuritis, and/or papilitis, by providing an effective amount of tacrolimus in a pharmaceutically acceptable formulation to a diseased eye. In one embodiment, the formulation is applied topically. In an alternative embodiment, the formulation is injected intraocularly, for example by subconjuctival, intravitreal, or retrobulbar injection. For subconjunctival injection a concentration in the range of about 1 ng/ml to 500 $\mu$g/ml tacrolimus may be used. For intravitreal injection a concentration in the range of 1–1000 $\mu$g/0.1 ml may be used, with a preferred concentration of about 50 $\mu$g/0.1 ml tacrolimus. For retrobulbar injection, a concentration in the range of about 20–1000 $\mu$g/ml tacrolimus may be used. Tacrolimus may be administered in an aqueous-based solution, for example tacrolimus bound to liposomes, or tacrolimus dissolved in an organic solvent. Tacrolimus may also be provided in an inert physiologically acceptable carrier by surgical implantation, injection, or topical application.

The invention is also directed to a composition for treating dry eye disease. The composition contains an effective amount of tacrolimus in a pharmaceutically acceptable formulation. The formulation may be an aqueous cream or liquid containing, for example, about 1 ng to 10 $\mu$g tacrolimus. The formulation may be an inert carrier such as a microsphere, liposome or polymeric matrix containing tacrolimus. Tacrolimus may be dissolved in an aqueous solvent such as 0.9% saline or 5% dextrose, or an organic solvent such as dimethylsulfoxide (DMSO) or an alcohol.

The invention is additionally directed to a composition for intraocular injection to treat ocular disease. An effective amount of tacrolimus is dissolved in either an aqueous solvent such as 0.9% saline or 5% dextrose, or an organic solvent such as DMSO or alcohol.

DETAILED DESCRIPTION

The invention is directed to a method and composition to treat ocular diseases by administration of tacrolimus (Prograf®, previously known as FK506). Tacrolimus, a macrolide immunosuppressant produced by *Streptomyces tsukubaensis*, is a tricyclo hydrophobic compound that is practically insoluble in water, but is freely soluble in ethanol and is very soluble in methanol and chloroform. It is available under prescription as either capsules for oral administration or as a sterile solution for intravenous administration. The solution contains the equivalent of 5 mg anhydrous tacrolimus in 1 ml of polyoxyl 60 hydrogenated castor oil (HCO-60), 200 mg, and dehydrated alcohol (USP, 80.0%$^{v/v}$), and must be diluted with a solution of 0.9% NaCl or 5% dextrose before use.

Tacrolimus may be administered in a topical formulation for treatment of ocular disease. In one embodiment, tacrolimus in amounts ranging from 1 ng to 10 μg is contained in an aqueous-based cream excipient. The drug may be incorporated directly into the cream in the same solution as used for intravenous administration, or may be contained in liposomes or microspheres either in solution or in an anhydrous form. The cream formulation is usually applied to the eye at bedtime, but it may be applied any time throughout the day if the cream does not cause blurred vision. Tacrolimus may also be applied topically in the form of eye drops using the same solution for intravenous administration.

Tacrolimus may also be injected intraocularly, using intravitreal, subconjunctival, or retrobulbar injection. For subconjctival injection, a dose in the range of 1 ng to 500 μg/ml may be used. For intravitreal injection, a dose in the range of 1–1000 μg/0.1 ml my be used, with a preferred dose of 50 μg/0.1 ml. For retrobulbar injection, a dose in the range of 20–1000 μg/ml may be used. The intravenous solution form of tacrolimus may be diluted to achieve the indicated concentration using 0.9% NaCl or 5% dextrose, or an organic solvent such as dimethylsulfoxide (DMSO) or alcohol, preferably a low molecular weight alcohol.

Tacrolimus may also be administered surgically as an ocular implant. As one example, a reservoir container having a diffusible wall of polyvinyl alcohol or polyvinyl acetate and containing milligram quantities of tacrolimus may be implanted in the sclera. As another example, tacrolimus in milligram quantities may be incorporated into a polymeric matrix having dimensions of about 2 mm by 4 mm, and made of a polymer such as polycaprolactone, poly(glycolic) acid, poly(lactic) acid, or a polyanhydride, or a lipid such as sebacic acid, and may be implanted on the sclera or in the eye. This is usually accomplished with the patient receiving either a topical or local anesthetic and using a small (3–4 mm incision) made behind the cornea. The matrix, containing tacrolimus, is then inserted through the incision and sutured to the sclera using 9–0 nylon.

Tacrolimus may also be contained within an inert matrix for either topical application or injection into the eye. As one example of an inert matrix, liposomes may be prepared from dipalmitoyl phosphatidylcholine (DPPC), preferably prepared from egg phosphatidylcholine (PC) since this lipid has a low heat transition. Liposomes are made using standard procedures as known to one skilled in the art. Tacrolimus in amounts ranging from nanogram to microgram quantities is added to a solution of egg PC, and the lipophilic drug binds to the liposome.

Tacrolimus bound with liposomes may be applied topically, either in the form of drops or as an aqueous based cream, or may be injected intraocularly. In a formulation for topical application, the drug is slowly released over time as the liposome capsule degrades due to wear and tear from the eye surface. In a formulation for intraocular injection, the liposome capsule degrades due to cellular digestion. Both of these formulations provide advantages of a slow release drug delivery system, allowing the patient a constant exposure to the drug over time.

As another example, tacrolimus may be dissolved in an organic solvent such as DMSO or alcohol as previously described and containing a polyanhydride, poly(glycolic) acid, poly(lactic) acid, or polycaprolactone polymer.

Tacrolimus may also be used to treat other conditions of the eye including uveitis (inflammation of the uvea), scleritis, (inflammation of the sclera), neuritis (inflammation of the optic nerve), or papilitis (inflammation of the optic nerve head) using the methods and formulations previously described. To treat uveitis, tacrolimus is preferably injected subconjuctivally at a dose in the range of 1 ng/ml to 50 μg/ml, or intravitreally at a dose of about 1–1000 μg/0.1 ml, preferably about 50 μg/0.1 ml. To treat scleritis involving the anterior sclera, tacrolimus is preferably administered topically. To treat scleritis involving the posterior sclera, tacrolimus is preferably administered by retrobulbar injection at a dose in the range of about 20–1000 μg/ml and dissolved in DMSO or a low concentration of alcohol. To treat neuritis or papilitis, tacrolimus is preferably administered by retrobulbar injection at a dose in the range of about 20–1000 μg/ml.

It should be understood that the embodiments of the present invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

What is claimed is:

1. A method of treating ocular disease comprising providing to a diseased eye a pharmaceutically acceptable formulation consisting essentially of an effective amount of tacrolimus for treating a disease selected from the group consisting of dry eye disease, scleritis, neuritis, papillitis, and combinations thereof.

2. The method of claim 1 wherein said formulation is applied topically.

3. The method of claim 1 wherein said formulation is injected intraocularly.

4. The method of claim 3 wherein said formulation is injected subconjutivally.

5. The method of claim 4 wherein said formulation contains about 1 ng/ml to 500 μg/ml tacrolimus.

6. The method of claim 3 wherein said formulation is injected intravitreally.

7. The method of claim 6 wherein said formulation contains about 1–1000 μg/0.1 ml tacrolimus.

8. The method of claim 3 wherein said formulation is injected retrobulbarly.

9. The method of claim 8 wherein said formulation contains about 20–1000 μg/ml tacrolimus.

10. The method of claim 3 wherein said formulation comprises tacrolimus in an aqueous-based solution.

11. The method of claim 10 wherein said aqueous-based solution contains tacrolimus bound to liposomes.

12. The method of claim 3 wherein said formulation comprises tacrolimus in an organic solvent.

13. The method of claim 3 wherein said formulation comprises liposomes with anhydrous tacrolimus.

14. The method of claim 1 wherein said formulation comprises tacrolimus contained in an inert carrier.

15. The method of claim 14 wherein said carrier containing tacrolimus is provided to said diseased eye by a method selected from the group consisting of surgical implantation, injection, and topical administration.

16. A method for treating ocular disease consisting of an intraocular injection of an effective amount of tacrolimus dissolved in a solvent selected from the group consisting essentially of an aqueous solvent and an organic solvent for injecting into an eye to treat a disease selected from the group consisting of dry eye disease, scleritis, neuritis, papillitis, and combinations thereof.

17. The method of claim 16 containing about 1 ng/ml to 1000 μg/ml tacrolimus.

18. The method of claim 16 wherein said aqueous solvent is selected from the group consisting of 0.9% NaCl and 5% dextrose.

19. The method of claim 16 wherein said organic solvent is selected from the group consisting of dimethylsulfoxide and alcohol.

* * * * *